(12) United States Patent
Bae

(10) Patent No.: US 6,866,653 B2
(45) Date of Patent: Mar. 15, 2005

(54) METHOD AND APPARATUS FOR SEQUENTIAL DELIVERY OF MULTIPLE INJECTABLE SUBSTANCES STORED IN A PREFILLED SYRINGE

(76) Inventor: Kyongtae T. Bae, 3 Fleetwood Dr., St. Louis, MO (US) 63124

( * ) Notice: Subject to any disclaimer, the term of this patent is extended or adjusted under 35 U.S.C. 154(b) by 129 days.

(21) Appl. No.: 10/285,001

(22) Filed: Oct. 31, 2002

(65) Prior Publication Data

US 2004/0097875 A1 May 20, 2004

(51) Int. Cl.$^7$ ................................................ A61M 5/00
(52) U.S. Cl. ......................... 604/191; 604/89; 604/205
(58) Field of Search ........................... 604/82, 89, 90, 604/91, 191, 200, 205

(56) References Cited

U.S. PATENT DOCUMENTS

| | | | |
|---|---|---|---|
| 978,488 A | * 12/1910 | Roesch | 604/204 |
| 4,439,184 A | 3/1984 | Wheeler | |
| 4,453,934 A | 6/1984 | Gahwiler et al. | |
| 4,496,344 A | 1/1985 | Kamstra | |
| 4,529,403 A | * 7/1985 | Kamstra | 604/136 |
| 4,715,854 A | * 12/1987 | Vaillancourt | 604/191 |
| 4,792,329 A | * 12/1988 | Schreuder | 604/90 |
| 4,861,335 A | * 8/1989 | Reynolds | 604/88 |
| 5,535,746 A | 7/1996 | Hoover et al. | |
| 5,583,902 A | 12/1996 | Bae | |
| 5,720,731 A | * 2/1998 | Aramata et al. | 604/191 |
| 5,743,886 A | 4/1998 | Lynn et al. | |
| 5,788,670 A | 8/1998 | Reinhard et al. | |
| 5,817,056 A | 10/1998 | Tanaka et al. | |
| 5,830,193 A | * 11/1998 | Higashikawa | 604/191 |
| 5,971,953 A | * 10/1999 | Bachynsky | 604/90 |
| 6,723,074 B1 | * 4/2004 | Halseth | 604/201 |
| 6,740,062 B2 | * 5/2004 | Hjertman | 604/187 |

* cited by examiner

*Primary Examiner*—Sharon Kennedy
(74) *Attorney, Agent, or Firm*—Thompson Coburn, LLP

(57) ABSTRACT

A syringe, which may be pre-filled, and a method of using the syringe is disclosed to provide sequential injection of two different fluids without mixing thereof. The syringe comprises in a first version a plunger and an intermediate disc sealingly disposed within a generally cylindrical barrel, with an outlet portion distal of the barrel, the outlet portion being generally larger in diameter so that as the disc is advanced into it far enough to substantially inject the first fluid the disc loses sealing engagement and the second fluid is then expelled around the disc and through the syringe opening. Baffles are provided within the outlet portion to prevent the disc from inadvertently sealing the opening, and channels may be provided around the baffles. In a second version a bag is provided adjacent the plunger, with the first fluid being contained within the barrel and the second fluid being contained within the bag, and at least one barb is provided in the bottom of the syringe to burst the bag after the first fluid is expelled to thereby expel the second fluid.

9 Claims, 7 Drawing Sheets

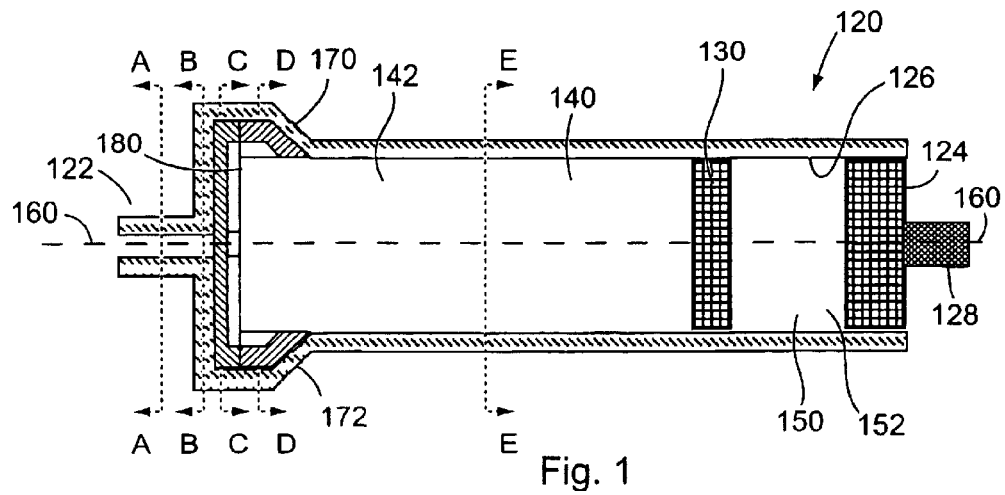
Fig. 1
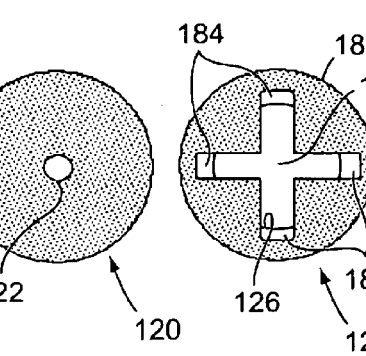
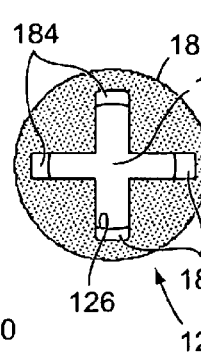
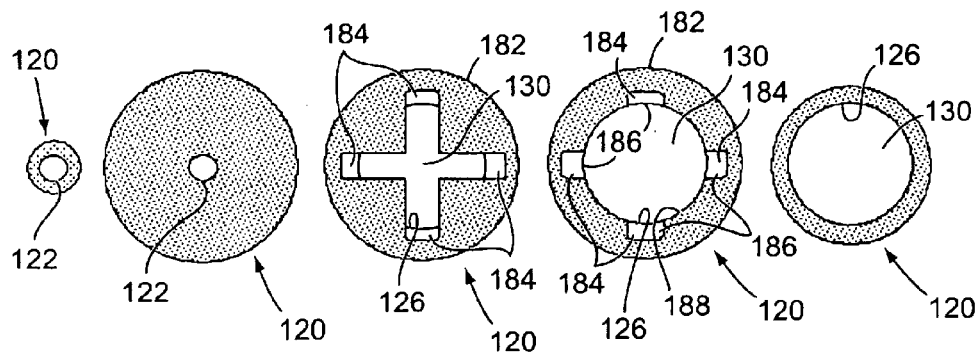
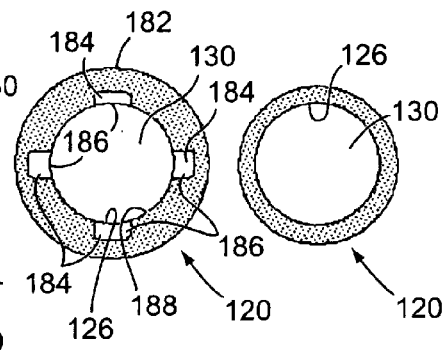
Fig. 1a   Fig. 1b   Fig. 1c   Fig. 1d   Fig. 1e
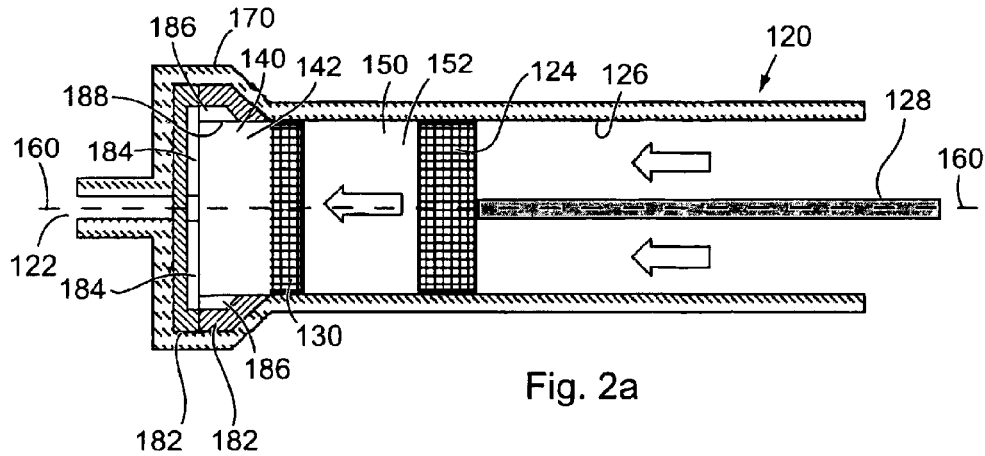
Fig. 2a

METHOD AND APPARATUS FOR SEQUENTIAL DELIVERY OF MULTIPLE INJECTABLE SUBSTANCES STORED IN A PREFILLED SYRINGE

FIELD OF THE INVENTION

This invention refers to a syringe, and more specifically, to a syringe used for the sequential administration of two different injectable substances which are stored in separate chambers in the syringe.

BACKGROUND OF THE INVENTION

Computed tomography (CT) is a widespread diagnostic imaging method which measures the x-ray attenuation coefficient of matter. This x-ray attenuation coefficient is depicted in terms of Hounsefield Units. During a CT scan, a collimated X-ray beam is directed on the patient and the attenuated remnant radiation is measured by a detector whose response is transmitted to a computer. The computer considers the location of the patient and the spatial relationship of the x-ray beam to the region of interest and analyzes the signal from the detector so that a visual image of the region of interest can be reconstructed and displayed on a monitor. The image can then be viewed or stored for later evaluation.

Hounsefields Units reflect the relative absorption of the CT x-rays by matter, where the absorption is related to the atomic number, electron density, physical thickness of the matter, and the energy spectrum of the x-rays. Because of the similarity in electron density of various tissues in the body, CT scans sometimes result in poor imaging. In an attempt to obtain better results in such circumstances, a contrast agent, such as iodine, can be injected in the patent's blood stream to change the relative radio-density of the tissues, and improve the overall diagnostic capabilities of the procedure.

In addition to CT, magnetic resonance imaging (MRI) is a clinically important medical imaging modality because of its exceptional soft-tissue contrast. MRI exploits the existence of induced nuclear magnetism in the patient body. The magnetic resonance signals from water and the hydrogen atoms in fat are mapped according to their location within the patient so that the internal organs of a patient can be imaged without the use of ionizing radiation. Since its development nearly 30 years ago, MRI has become an invaluable medical imaging modality. Just like CT, contrast enhancement is extremely valuable in MRI for the visualization of normal tissue as well as the diagnosis of soft tissue diseases. Although there is an intrinsic contrast between a lesion and surrounding tissue in MRI, it is critical to selectively enhance the pathology or the structure of interest by administering a contrast agent. The most common agent used in MRI is Gadolinium, which can dramatically improve the conspicuity of the lesion and the image quality, particularly in magnetic resonance angiography.

The volume of Gadolinium used in a typical MRI procedure is usually around 20 cc, which is one-fifth of the amount of iodonated contrast used in a typical CT procedure. Because of this small volume, the relative amount of Gadolinium remaining in an injection tubing after completion of the injection is substantial. To prevent waste, it is important to completely inject any Gadolinium remaining in the tubing at the completion of injection.

Contast agents may be administered either manually through hand injection of a syringe or automatically through the use of power injection equipment. Several manufacturers, including Mallinckrodt Medical Inc. and MedRad Inc., produce a wide variety of power injectors for use in both CT and MR procedures. These power injectors may be either a single barrel style for injection of one syringe as in most of CT injectors or double barrel style for injection of two syringes as in most of MRI injectors, although the single barrel style tends to be more commonly used.

Contrast agents are typically provided in a bottle and are drawn into a syringe immediately prior to use in either manual or power injection imaging procedures. In applications where a relatively small volume of contrast agent is used, such as in an MR imaging procedure using Gadolinium, injection of the contrast agent may be performed by manual injection with a common syringe with injection tubing and an angiocatheter placed in the arm. In other applications, the syringe may be manually prepared for use in a power injector. As with any manual procedure, manual preparation of syringes involves multiple steps that are time-consuming and associated with potential contamination problems and dosing errors.

To alleviate the problems inherent in manually preparing syringes of contrast agent, some suppliers provide contrast agents in prefilled syringes that can be used in either manual or power injection procedures. The prefilled syringe is gaining wide acceptance because it can reduce the complications and the number of steps previously associated with using bottled contrast agents, and a recent survey by the American Society of Radiologic Technologists reported that using a prefilled syringe in power injection equipment resulted in improved efficiency and quality of service, and less wasted contrast agent.

In CT and MR imaging procedures, the injection of a contrast agents maybe followed by the injection of a saline solution, which is commonly referred to as a saline flush or saline chase. The saline injection has several advantages in that it reduces the amount of contrast agent used and prevents waste. Previously, when planning an imaging procedure, the amount of contrast agent to be injected had to be increased to compensate for the amount of contrast agent left in the injection tubing at the completion of the procedure between the syringe and the patient vascular access injection site. Ordinarily, this amount of contrast agent is discarded along with the injection tubing at the end of the procedure. However, by using the saline flush, almost all of the contrast agent in the syringe can be used because the contrast agent that remains in the injection tubing between the injector and the patient vascular access injection site is injected into the body with the saline flush. The saline flush is also beneficial because it provides a final push and continuous steady flow of the contrast agent that is slowly flowing in the peripheral blood stream at the tail end of the injection, thereby improving efficient use and diagnostic contribution of the contrast agent that is already injected into the body. The saline flush also disperses the contrast agent accrued in the central venous structures at the tail end of the injection to reduce associated artifact at the injection site. Finally, injecting 10–20 cc saline after the completion of a contrast CT study is a standard practice to clear up any residual contrast agent which may clog the vascular access site because of its high viscosity.

Despite its known benefits, the injection of a saline bolus immediately following the contrast agent is not commonly practiced. Most often, the saline flush injection is administered by using a double barrel power injector that can inject two syringes independently and sequentially. In the double barrel injector, one of the injector barrels is used for injecting the contrast agent and the other injector barrel is used for injecting the saline flush solution. In a double barrel power injector set-up, each of the syringes in the injector has a tubing that leads from the syringe to a one-way valve and then to a Y-adapter which then leads to a common injection catheter. The double barrel power injector allows for a precise amount of contrast agent to be injected from the first syringe at a steady and continuous injection rate followed immediately by the injection of saline from the other syringe. Without a double-barrel injector, injection may be performed manually, but a manual injection cannot provide the precise injection rate required to produce good-quality images, particularly when CT contrast agent is injected, which tends to be very viscous. Additionally, with manual injection, it is often difficult to inject the saline flush rapidly and immediately after injection of the contrast agent without any gaps in the bolus. Because most CT power injectors are of the single barrel style, a saline flush is typically not performed. Thus, to provide the benefits of the saline injection after the injection of the contrast agent, what is needed is a single pre-filled syringe that stores both substances separately and can inject them sequentially either manually or through existing single barrel power injection equipment.

In the medical field, a dual chamber prefilled syringe has been commonly used to separately store two substances, usually a medical component and a vehicle. However, these syringes do not allow for sequential injection of the substance, but are intended to provide a thorough mixing of the substances into a homogeneous injection liquid before injection. In the syringes described in U.S. Pat. Nos. 5,788,670 and 5,865,799, the two substances are mixed within the prefilled syringe and then directly injected from the prefilled syringe. Typically, the dual chamber prefilled syringe is formed of a single syringe barrel made of glass or plastic with an end plunger and rod positioned opposite of the syringe head. An intermediate plunger is positioned in the barrel of the syringe to divide the barrel of the syringe and create two separate chambers in the syringe for separately storing the substances before injection. When injecting the contents of the syringe, the plunger rod connected to the plunger is moved forward in the direction of the syringe head thereby forcing the intermediate plunger through the syringe until it reaches a bypass positioned in the mid section of the syringe barrel, which allows the substance in the second chamber to flow into the first chamber where the two components are then subsequently mixed and injected by the continued movement of the plunger and plunger rod. While conventional syringes of this type are effective for mixing two substances immediately before injection to reduce the risk of cross contamination and to allow effective packaging of the substances, conventional syringes of this type do not allow for sequential injection of the components in the syringe so as to allow their use in an imaging application with saline flush as described above.

What is needed is a syringe capable of sequentially injecting two substances from one syringe. Such a syringe would be readily useable in imaging applications as the syringe would be preferably pre-filled with a desired contrast agent and a saline solution to provide in-line flushing in the injection tubing to prevent waste of the contrast agent even when small volumes of contrast agent are used. Such a syringe would be readily adaptable to fit in existing power injection equipment such as the commonly used single barrel injector described previously or a double barrel injector where only one side of the injector need be used. By providing the flush solution in line with the contrast agent, all of the contrast agent in the tube can be used instead of discarding the residual contrast agent that is ordinarily left over in the injection tubing in the double barrel injector between the syringe head and the "Y" connector or in the single barrel injector between the syringe head and the patient injection site. Such a syringe would allow the use of a saline flush with the single barrel injector to achieve the clinical benefits described above that are ordinarily only achieved through the use of the less common double barrel injector.

SUMMARY OF THE INVENTION

Among the aspects of the present invention is the provision of dual chamber syringe that is adapted to provide sequential injection of two substances from one syringe. Preferably, the syringe has a first chamber for holding a first fluid and a second chamber separate from the first chamber for holding a second fluid. An outlet is provided though which the fluids stored in the first and second chambers flow during injection. During injection, the outlet first communicates solely with the first chamber to allow the first chamber fluid to be injected from the syringe after which the outlet communicates with the second chamber to allow the second chamber fluid to be injected.

Preferably, the outlet of the syringe is on an end of the syringe and the syringe has a moveable plunger that is connected to a plunger rod at an end opposite the outlet. The plunger rod may be pushed forward, thereby advancing the first chamber fluid and the second chamber fluid through the syringe. This action of the plunger allows the first fluid to be injected first, and then allows the second fluid to be injected only after completion of the injection of the first fluid. A syringe constructed in accordance with this aspect of the invention may used in an imaging application by placing a contrast agent in the first chamber and a saline solution in the second chamber. By forward advancement of the plunger, the saline solution pushes the contrast agent into the patient injection site and then itself flows into the patient injection site to provide the benefits described above.

In one aspect of the invention, the first and second chambers and the fluids stored therein are separated by a movable intermediate plunger or disc disposed within the syringe interior. During injection, the disc sealingly contacts or engages the syringe interior to separate the chambers and their respective fluids. As the disc moves through the tube interior, the disc acts on the first chamber fluid to inject the first chamber fluid. After substantial completion of the injection of the first fluid, the disc disengages from the syringe interior to bring the outlet into communication with the second chamber to allow injection of the second fluid. Preferably, the syringe is configured to engage the disc as its travels to the outlet, and the outlet is configured to disengage the disc from the syringe interior after the first fluid has been substantially evacuated from its chamber to bring the outlet into communication with the second chamber, thereby achieving sequential injection of the first and second fluids. There are various syringe embodiments disclosed for achieving this disengagement, preferably with a substantially cylindrical barrel having an outlet with an asymmetric shape or arrangement such that a disc of regular or circular shape will remain sealed until it comes into discontinuity with the outlet by being advanced thereinto. This discontinuity creates a bypass around the disc, through which the second fluid will be brought into communication with the outlet opening, thereby allowing it to be injected.

In another aspect of the invention, the second chamber may comprise a sealed bag disposed in the syringe and the second fluid may be contained in the bag thereby separating the first and second fluids in the syringe. In accordance with this aspect of the invention, the outlet is configured to pierce the bag after the first fluid has been substantially injected thereby releasing the second fluid from the bag and allowing the second fluid to be injected sequentially after the first fluid.

Other aspects and provisions of the invention will become apparent upon further review of the drawings figures showing different embodiments of syringes of the present invention and in the detailed description thereof which follows.

BRIEF DESCRIPTION OF THE DRAWINGS

FIG. 1 is a longitudinal cross-sectional view of a syringe comprising a first embodiment of the present invention;

FIG. 1A is a transverse cross-sectional view of the syringe along lines A—A of FIG. 1 detailing the outlet opening of the syringe;

FIG. 1B is a transverse cross-sectional view of the syringe along lines B—B of FIG. 1 detailing the bottom of the syringe outlet;

FIG. 1C is a transverse cross-sectional view of the syringe along lines C—C of FIG. 1 detailing the baffle formed in the bottom of the syringe;

FIG. 1D is a transverse cross-sectional view of the syringe along lines D—D of FIG. 1 detailing the channels around the baffle;

FIG. 1E is a transverse cross-sectional view of the syringe along lines E—E of FIG. 1 detailing the generally cylindrical shape of the syringe barrel and intermediate disc;

FIGS. 2A–C are longitudinal cross-sectional views of the syringe of FIG. 1. illustrating the intermediate steps of injection for the syringe of FIG. 1;

Corresponding reference characters indicate corresponding parts throughout the several views of the drawings.

DETAILED DESCRIPTION OF THE PREFERRED EMBODIMENT

Mode I

Figure 2B:
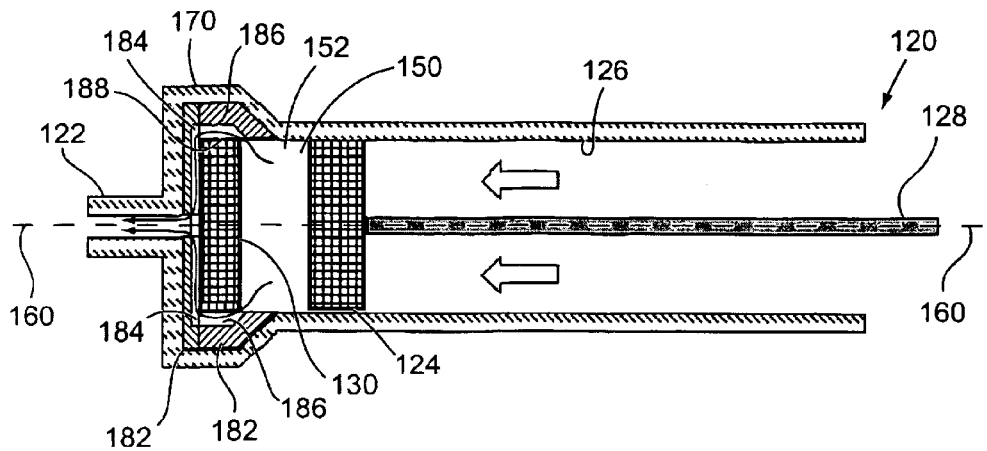

FIGS. 1, 1A–1E and 2A–2C show one embodiment of a syringe 120 of the present invention, which will be referred to hereinafter as Mode I. The syringe of Mode I comprises a preferably, generally, cylindrical barrel or tube preferably having an outlet 122 at one end and a plunger 124 at an end opposite the outlet. The plunger 124 has sealing contact or engagement with an interior sidewall 126 of the tube to allow it to be moved along a length of the tube toward the outlet 122 and to provide the necessary force to inject a contents of the syringe from the outlet, as will be described in greater detail below. A rod 128 may be attached to the rear plunger 124 to move the rear plunger 124 along preferably the entire length of the tube.

An intermediate plunger or disc 130 is provided in the tube interior to divide the tube into a first chamber 140 for holding a first contents 142 and a second chamber 150 for holding a second contents 152. The first chamber 140 is defined by the space in the tube interior between the disc 130 and the outlet 122 and the second chamber 150 is defined by the space in the tube interior between the disc and the rear plunger 124. The disc 130 sealingly contacts or engages with the barrel portion of the tube interior 126 to prevent mixing of the chambers' contents or fluids 142,152 when the syringe 120 is stored prior to use and also when the first chamber is being compressed and the first chamber contents 142 is being injected. As will be described in greater detail below, when the syringe is filled, the disc 130 moves along a portion of the length of the tube through the action of the plunger 124 acting on the second chamber contents 152. This in turn causes the disc 130 to push on the first chamber contents 142 to provide injection while at the same time preventing the mixing of the chambers' contents 142,152. Preferably, the outlet 122 and the first and second chambers 140,150 are aligned axially along a center axis 160—160 of the tube, and preferably, the plunger 124 and the disc 130 are aligned axially with the outlet and the first and second chambers such that the disc and plunger act directly on the first and second chambers and their contents, respectively.

Preferably, the Mode I syringe 120 is formed with a radially enlarged outlet portion 170 or vestibule adjacent the outlet 122. The radially enlarged outlet portion 170 may be formed as a protruding ring at the syringe outlet such that an exterior surface 172 of the tube has a larger outer diameter at the radially enlarged outlet portion or the radially enlarged outlet portion may be formed within a wall thickness of the tube thereby allowing the tube exterior to have a uniform outer diameter. Preferably, the radially enlarged outlet portion 170 extends completely around the tube so as to accommodate a baffle 180 at the outlet 122 of the syringe, as will be described below. This radially enlarged outlet portion or vestibule 170 forms a discontinuity in the tube or barrel whereat the disc falls out of sealing engagement therewith, as explained below.

Preferably, the baffle 180 is disposed within the radially enlarged outlet portion 170 and provides a means of preventing the disc 130 from obstructing or sealing the outlet opening 122 when the disc moves towards the outlet after injection of the first chamber contents 142. Preferably, the baffle 180 allows the second chamber contents 152 to flow from the second chamber 150 to the outlet opening 122 when the disc 130 is moved towards the outlet into the radially enlarged outlet portion 170 of the syringe. As shown in FIGS. 1B–1C, the baffle 180 is arranged in the bottom of the syringe to engage the disc 130 at a distance from the outlet opening sufficient to allow the second chamber contents to flow to the outlet opening 122 through channels 184 in the baffle. The baffle may be a single piece of material or may be formed by layers 182 of material each having different geometric cross sections which the create the channels 184 to the outlet 122 when stacked axially. As shown in FIG. 1D, the baffle has notches 186 around a bore 188. Thus, when the disc 130 moves into the radially enlarged portion 170 and the bore 188 receives the disc, the notches 186 provided in the layers 182 of FIGS. 1B–1C allow the second chamber contents 152 to flow around the disc in the channels 184 to the outlet 122. For example, in the arrangement shown in FIGS. 1B–1D, the layers 182 create a baffle with four channels 184 that lead to the outlet 122 when the disc is received in the baffle bore 188. Preferably, the radially enlarged outlet portion 170 is sized to receive each of the layers 182 comprising the baffle 180 and provide a smooth transition for the disc 130 when it moves from the tube interior 126 to the baffle bore 188.

Figure 2C:
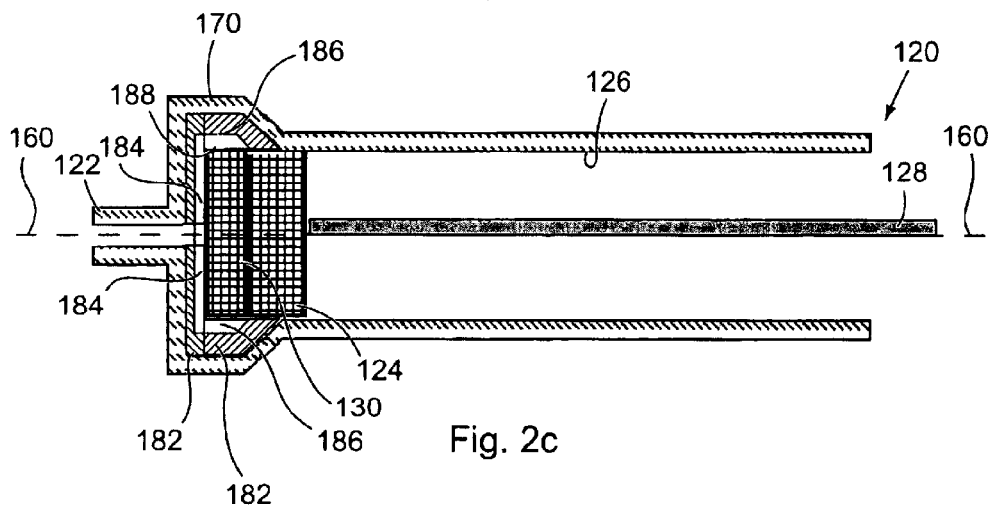

Referring to FIGS. 2A–2C which show the operation of the Mode I syringe 120, two different injectable substances 142,152 are stored separately in the first and second chambers 140,150 of the syringe. With the plunger 124 pushed forward, the contents of the first chamber 140 is injected first through the outlet opening 122 through the action of the plunger acting on the second chamber contents 152 which in turn acts on the disc 130 and the first chamber contents 142. Following the completion of the injection of the first chamber contents 142, the disc 130 is received in the baffle bore 188 (FIG. 2C). In this position, the disc 130 is fully engaged against the baffle but the channels 184 remain open between the disc and the baffle 180 such that the second chamber contents 152 flows through the notches 186 into the channels to the outlet opening 122. Thus, as the rear plunger is advanced until it abuts the disc 130, the second chamber contents 152 continues to flow to the outlet opening 122 though the channels 184 formed between the disc 130 and the baffle 180 until the second chamber 150 is sufficiently compressed and the remaining second chamber contents is fully injected from the syringe. In this position, a portion of rear plunger 124 may also be received in the baffle bore 188. As shown in FIG. 2C, the rear plunger 124 preferably has its axial width or thickness dimensioned so that at the end of the injection with the plunger 124 against the disc 130, the radially enlarged outlet portion 170 of the tube remains sealed at the rear opening of the syringe.

In summary, the disc remains in sealing engagement with the syringe sidewall as it traverses the barrel portion, but loses its seal as it enters the outlet portion of the syringe and encounters the discontinuity present there, preferably containing a baffle. The baffle blocks the possibility of the disc interfering with the flow of the second contents through the syringe and out the outlet opening.

Mode II

FIGS. 3, 3A–3E and 4A–4C show an alternate embodiment of a syringe 220 of the present invention, which will be referred to hereinafter as Mode II. The Mode II syringe 220 also comprises a preferably, generally, cylindrical tube barrel preferably having an outlet 222 at one end and a plunger 224 at the opposite end. The plunger 224 is sealingly engaged with the tube interior 226 and moves along the tube length toward the outlet 222 to provide the needed force to inject the syringe contents from the outlet. Preferably, the outlet 222 and the first and second chambers 240,250 are aligned axially along the center axis 260—260 of the tube, and preferably, the plunger 224 is aligned axially with the outlet and the first and second chambers such that the plunger acts directly on the second chamber and its contents. As in Mode I, the Mode II syringe has an intermediate movable plunger or disc 230 that is sealingly engaged with the tube interior 226 to define the first and second chambers 240,250 and to maintain the separation of the chambers' contents 242,252 during storage and through a first part of the injection.

Figure 3:
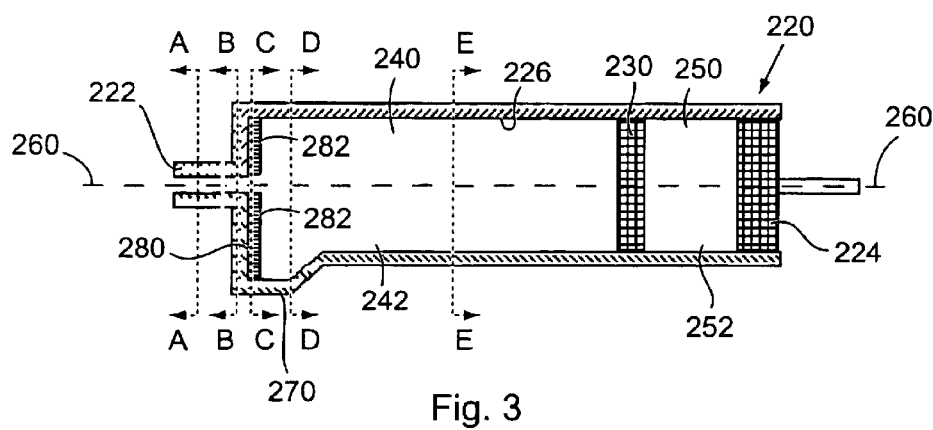
FIG. 3 is a longitudinal cross-sectional view of an alternate embodiment of the syringe of the present invention.
Figures 3A, 3B, 3C, 3D, 3E:
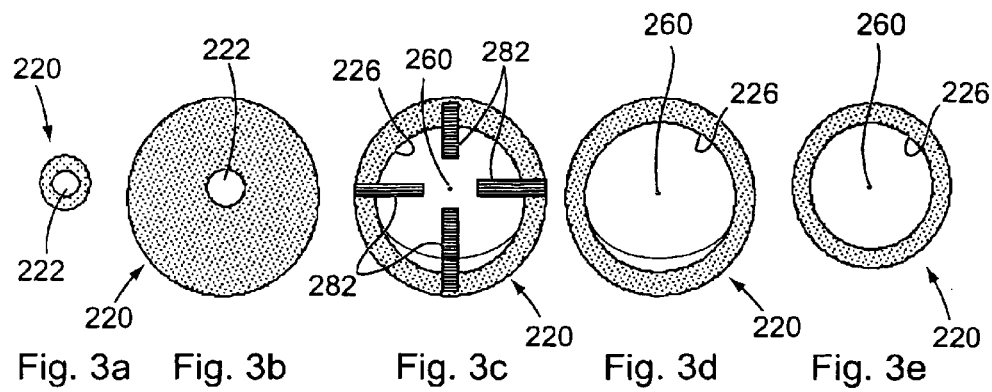
FIG. 3A is a transverse cross-sectional view of the syringe along lines A—A of FIG. 3 detailing the outlet opening of the syringe.
FIG. 3B is a transverse cross-sectional view of the syringe along lines B—B of FIG. 3 detailing the bottom of the syringe outlet with the off-center outlet opening.
FIG. 3C is a transverse cross-sectional view of the syringe along lines C—C of FIG. 3 detailing the baffle formed in the bottom of the syringe.
FIG. 3D is a transverse cross-sectional view of the syringe along lines D—D of FIG. 3 detailing the channel around the disc.
FIG. 3E is a transverse cross-sectional view of the syringe along lines E—E of FIG. 3 detailing the generally cylindrical shape of the syringe barrel and intermediate disc.

The main body of the syringe has a radially enlarged outlet portion 270 adjacent the outlet opening 222 at the front of the tube. Preferably, in Mode II, the radially enlarged portion 270 only extends around a portion of the tube and may be formed within the wall thickness of the tube to allow the tube to have a uniform outer diameter or as a protuberance such that the tube has an enlarged outer diameter in the area adjacent the outlet. Preferably, the radially enlarged outlet portion 270 has a generally circular cross section with its center offset from the center axis of the tube (FIG. 3B).

Preferably, a baffle 280 is disposed in the radially enlarged outlet portion 270 to engage the disc 230 and hold the disc away from the outlet opening 222 to prevent obstruction of the outlet and to allow the second chamber contents 252 to flow around the disc and out of the syringe. As shown in FIG. 3C, the baffle 280 comprises preferably four rectangular members 282 which extend radially from the radially enlarged outlet portion 270 of the tube interior toward the tube center where the ends of the members 280 in the center of the tube are spaced from one another to provide an unobstructed path to the outlet 222.

Figure 4A:
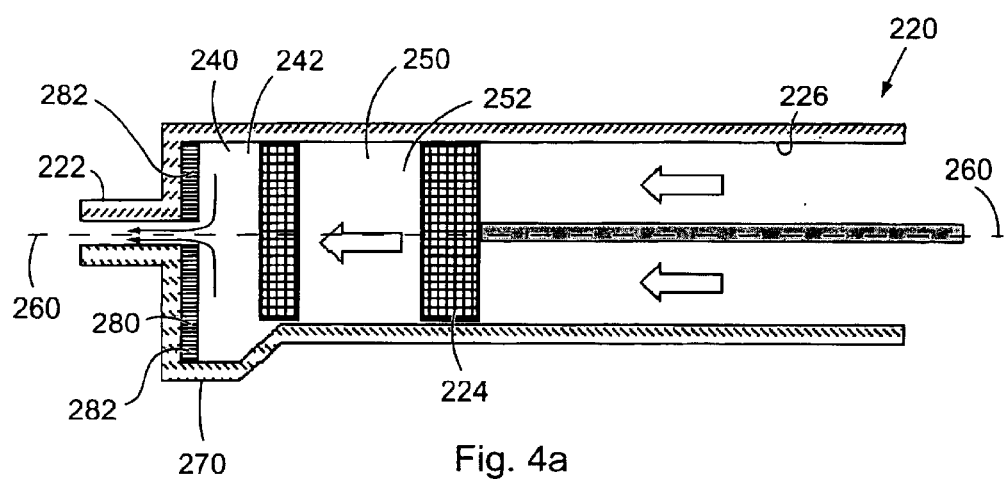
FIGS. 4A–C are longitudinal cross-sectional views of the syringe of FIG. 3 illustrating the intermediate steps of injection for the syringe of FIG. 3.
Figure 4B:
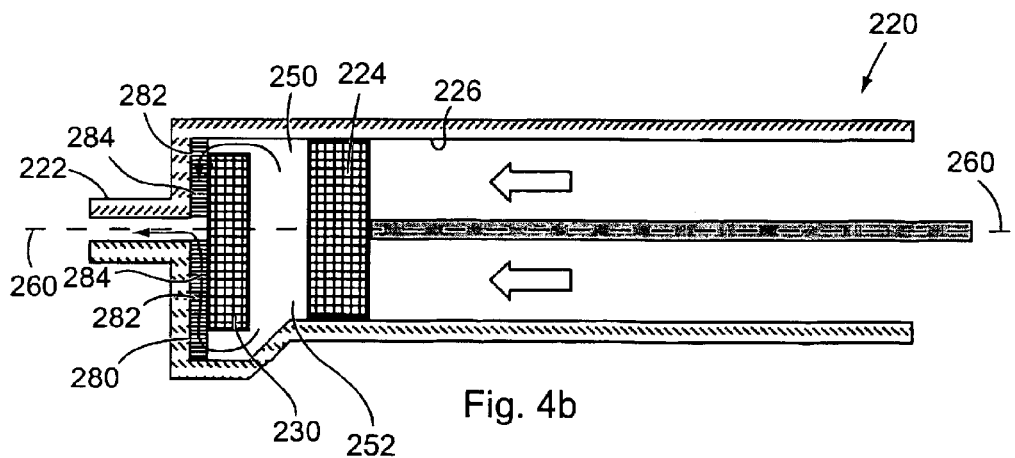
Figure 4C:
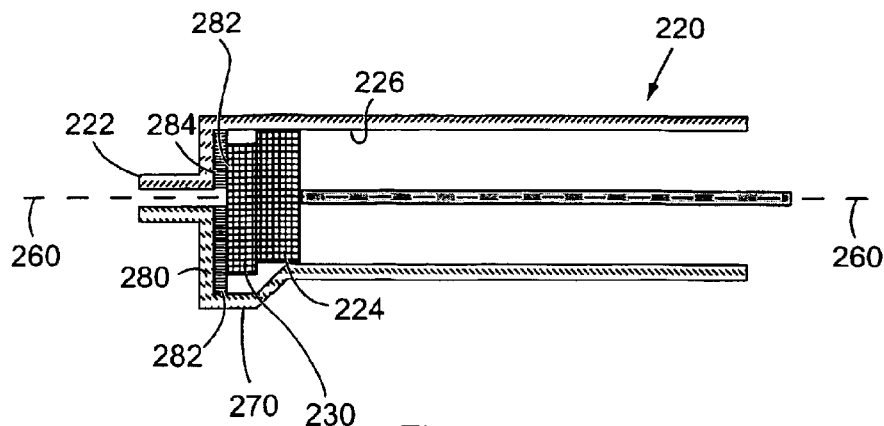

Referring to FIGS. 4A–4C which show the operation of the Mode II syringe 220, forward motion of the rear plunger 224 pushes the second chamber contents 252 and the disc 230 through the tube interior, resulting in the injection of the first chamber contents 242. After substantially completing injection of first chamber contents 242, the disc 230 enters the radially enlarged outlet portion 270. Because the diameter of the radially enlarged outlet portion 270 is greater than that of the disc 230, when the disc approaches the radially enlarged portion, the disc becomes disengaged from the tube interior 226 allowing the second chamber contents 252 to flow around the disc (FIG. 4B). The disc 230 then tends to become centered in the radially enlarged outlet portion 270 from the flow of the second chamber contents 252 around the disc. As the disc 230 moves toward the outlet 222, the baffle 280 prevents the disc from completely obstructing the syringe outlet opening. The second chamber contents 252 continues to flow around the disc and the baffle rectangular members 282 to the outlet opening 222 until the rear plunger 224 comes to rest against the disc, thereby completing the injection of the second fluid. In this position, the rear plunger 224 has its width or thickness dimensioned so that at the end of the injection of the second chamber contents 252, the radially enlarged outlet portion 270 of the tube interior remains sealed to the rear opening of the syringe (FIG. 4C).

As with Mode I, in Mode II the intermediate disc remains in sealing engagement with the syringe sidewall as it traverses the barrel portion, but loses its seal as it enters the outlet portion of the syringe and encounters the discontinuity present there, preferably containing a baffle. The baffle blocks the possibility of the disc interfering with the flow of the second contents through the syringe and out the outlet opening.

Mode III

FIGS. 5, 5A–5E, and 6A–6C show an alternate embodiment of a syringe 320 of the present invention which will hereinafter be referred to as Mode III. Again, the overall construction and operation of the Mode III syringe 320 is similar to that of Modes I and II described above. The disc 330 is sealingly engaged with the tube interior 326 to divide the tube into first and second chambers 340,350 while maintaining the separation of the chambers' contents 342, 352 during its storage and first part of the injection. Preferably, the first and second chambers 340,350 are aligned axially with the syringe outlet 322 along the center axis 360—360 of the syringe interior, and preferably, the disc 330 and the rear plunger 324 are aligned axially along the center axis of the syringe interior.

Figure 5:
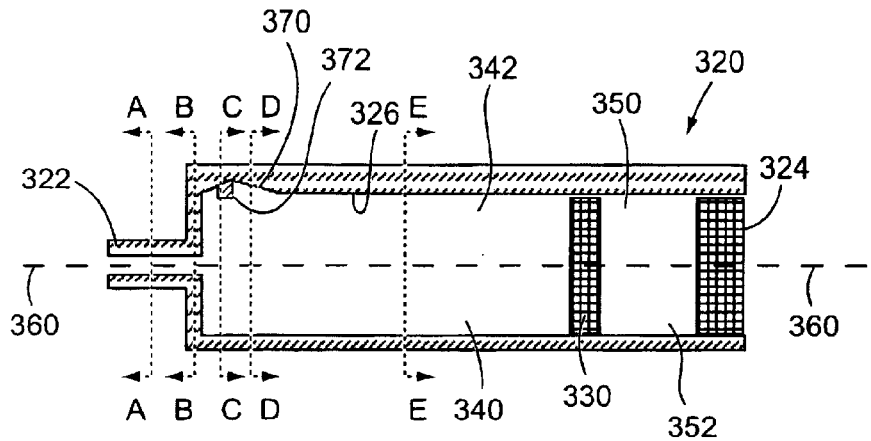
FIG. 5 is a longitudinal cross-sectional view of still another alternate embodiment of the syringe of the present invention.
Figures 5A, 5B, 5C, 5D, 5E:
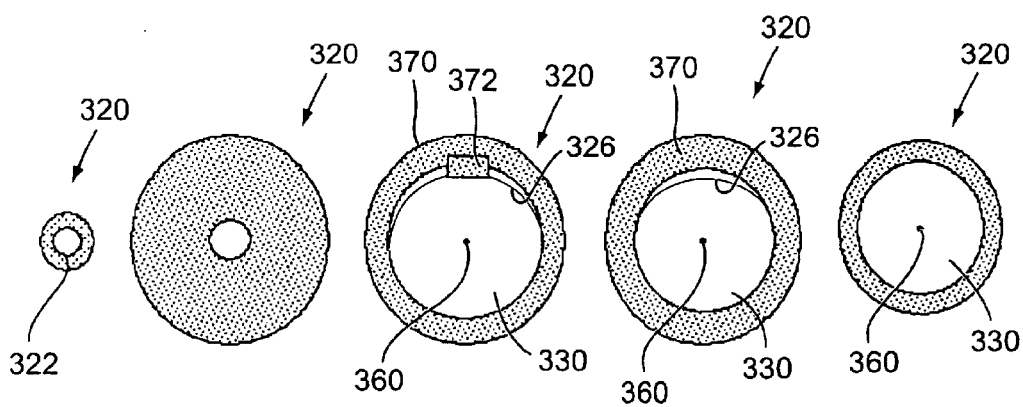
FIG. 5A is a transverse cross-sectional view of the syringe along lines A—A of FIG. 5 detailing the outlet opening of the syringe.
FIG. 5B is a transverse cross-sectional view of the syringe along lines B—B of FIG. 5 detailing the bottom of the syringe outlet with the outlet opening.
FIG. 5C is a transverse cross-sectional view of the syringe along lines C—C of FIG. 5 detailing the baffle or protrusion formed in the sidewall of the syringe outlet.
FIG. 5D is a transverse cross-sectional view of the syringe along lines D—D of FIG. 5 detailing the channel around the disc.
FIG. 5E is a transverse cross-sectional view of the syringe along lines E—E of FIG. 5 detailing the generally cylindrical shape of the syringe barrel and intermediate disc.

The syringe 320 has its radially enlarged outlet portion 370 formed adjacent the outlet opening 322 at the front of the tube. As with the Mode II syringe, the Mode III syringe preferably has its radially enlarged outlet portion 370 that only extends around a portion of the tube. The radially enlarged outlet portion 370 may be formed within the wall thickness of the tube to allow the tube to have a uniform outer diameter or the radially enlarged portion may be formed as a protuberance such that the tube has an enlarged outer diameter in the area adjacent the outlet opening 322. Preferably, the radially enlarged outlet portion 370 has a generally circular cross section with its center offset from the center axis 360—360 of the tube (FIG. 5C). Preferably, centered within the radially enlarged portion 370, a baffle comprising a protrusion 372 is provided that extends partially in a radial direction from the tube wall toward the tube interior. Preferably, the protrusion 372 has a relatively short arc length within the radially enlarged portion, as will become apparent from the description below. The radially enlarged outlet section 370 is configured to allow the disc 330 to be tilted or partially rotated when the disc travels into the radially enlarged outlet section and engages the protrusion 372.

Figure 6A:
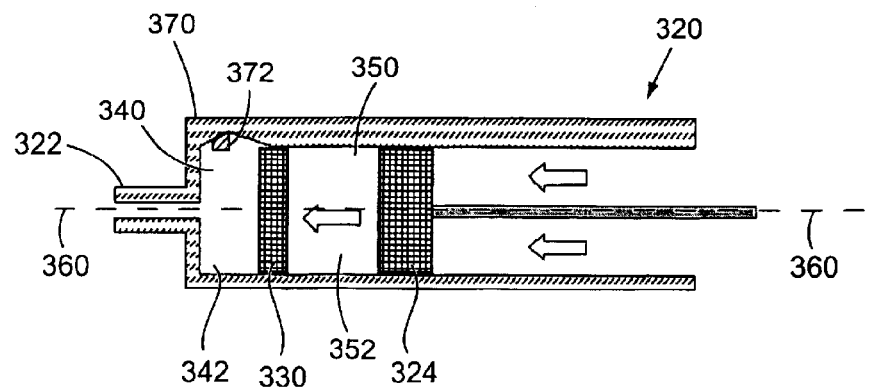
FIGS. 6A–C are longitudinal cross-sectional views of the syringe of FIG. 5 illustrating the intermediate steps of injection for the syringe of FIG. 5.
Figure 6B:
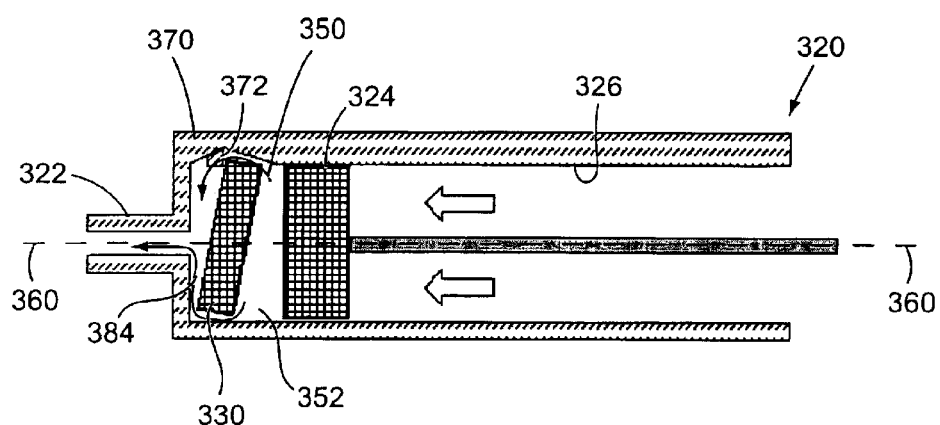
Figure 6C:
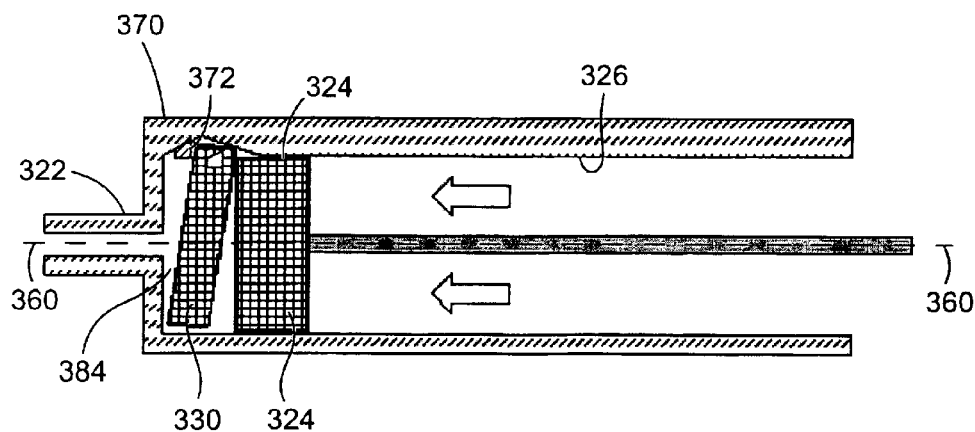
Figure 7:
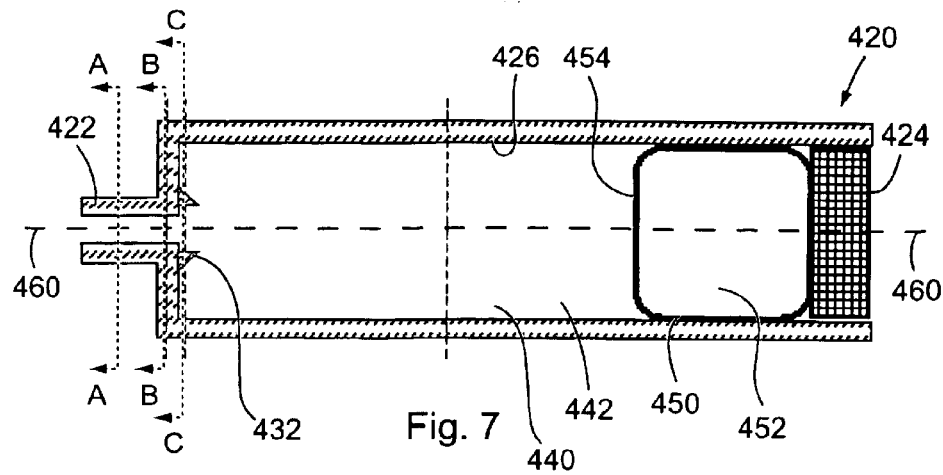
FIG. 7 is a longitudinal cross-sectional view of yet another alternate embodiment of the syringe of the present invention.
Figures 7A, 7B, 7C:
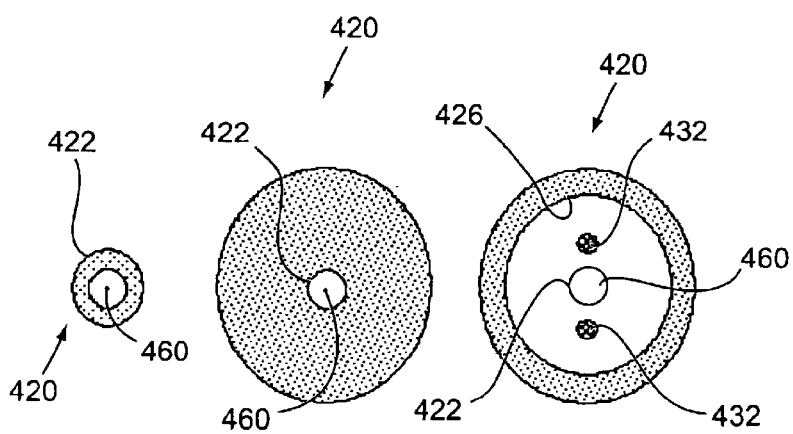
FIG. 7A is a transverse cross-sectional view of the syringe along lines A—A of FIG. 7 detailing the outlet opening of the syringe.
FIG. 7B is a transverse cross-sectional view of the syringe along lines B—B of FIG. 7 detailing the bottom of the syringe outlet with the outlet opening.
FIG. 7C is a transverse cross-sectional view of the syringe along lines C—C of FIG. 7 detailing the barbs or protrusions formed in the bottom of the syringe outlet.

Referring to FIGS. 6A–6C which show the operation of the syringe of Mode III, forward motion of the rear plunger 324 pushes the second chamber contents 352 and the disc 330, resulting in the injection of the first chamber contents 342 (FIG. 6A). After the completion of the injection of the first chamber contents 342, the disc 330 enters the radially enlarged outlet portion 370 and engages the protrusion 372 whereupon the disc is tilted by the continued forward motion of the rear plunger 324 and from the flow of the second chamber contents 352 to the outlet. This tilting causes the disc 330 to lose its sealing engagement with the tube. The disc 330 becomes trapped in the radially enlarged outlet portion 370, but because the disc is disengaged from the tube interior 326 as it is tilted or partially rotated, the second chamber contents 352 flows around the disc to the outlet 322 in the channels 384 created between the disc, the protrusion 372 and the radially enlarged outlet portion. The second chamber contents 352 continues to flow around the disc until the second chamber contents is fully injected when the rear plunger 324 comes to rest against the disc. In this position, the rear plunger 324 has its width or thickness dimensioned so that at the end of the injection of the second chamber contents 352, the radially enlarged portion 370 of the tube interior remains sealed to the rear opening of the syringe (FIG. 6C).

As in Modes I and II, in Mode III the intermediate disc remains in sealing engagement with the syringe sidewall as it traverses the barrel portion, but loses its seal as it enters the outlet portion of the syringe and encounters the discontinuity present there, preferably containing a baffle. The baffle blocks the possibility of the disc interfering with the flow of the second contents through the syringe and out the outlet opening.

Mode IV

FIGS. 7, 7A–7C, and 8A–8C show an alternate embodiment of a syringe 420 of the invention which will hereinafter be referred to as Mode IV. The Mode IV syringe 420 is a cylindrical tube preferably having its outlet 422 at one end and its plunger 424 at an end opposite the outlet. The plunger 424 is sealingly engaged with an interior 426 of the tube to allow it to be moved along a length the of tube toward the outlet 422 and to provide the necessary pressure to inject a contents of the syringe from the outlet. In the Mode IV syringe 420, the outlet 422 is configured with one or more barbs 432, the purpose of which will be described in greater detail below.

In the Mode IV syringe, a bag 450 is disposed in the tube interior 426 adjacent the rear plunger and filled with a contents 452. The structure of the bag divides the syringe into the first and second chambers 440,450 where a front wall 454 of the bag primarily applies a force on the first chamber 440 during injection of the first chamber contents 442. The bag 450 may be generally cylindrical in shape and generally conform to the tube interior 426 although it is not necessary that the bag sealingly engage the tube interior as the chamber contents are kept separate through the integrity of the bag 450. In this way, the rear plunger 424 may act on the first chamber contents 442 directly, although the bag 450 and primarily its front wall 454 will also act on the first chamber 440 as the bag is guided through the tube by the rear plunger. The bag 450 may also be attached or adhered to the rear plunger 424 to ensure the bag remains aligned and adjacent the rear plunger 424 in the tube and to provide the consistent application of positive pressure by the rear plunger during injection. Preferably, the syringe outlet 422, the rear plunger 424 and the first chamber 440 are aligned axially with the center axis 460—460 of the syringe.

Figure 8A:
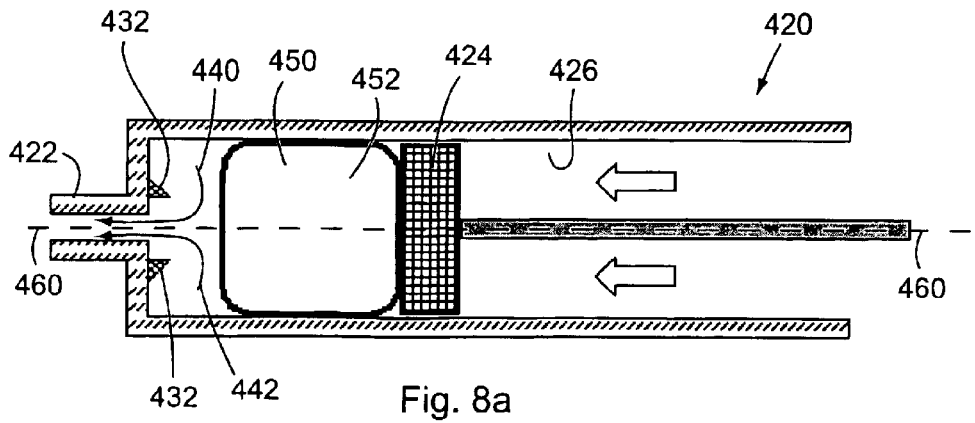
FIGS. 8A–C are longitudinal cross-sectional views of the syringe of FIG. 7 illustrating the intermediate steps of injection for the syringe of FIG. 7.
Figure 8B:
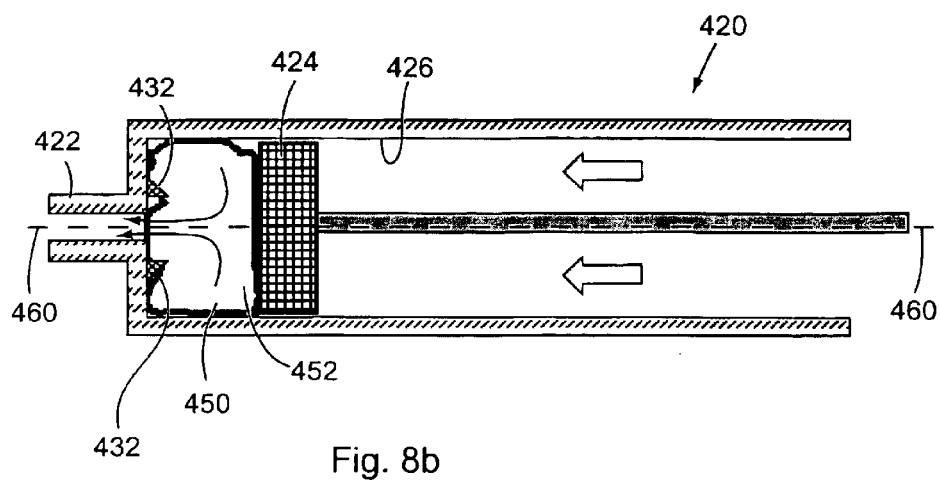
Figure 8C:
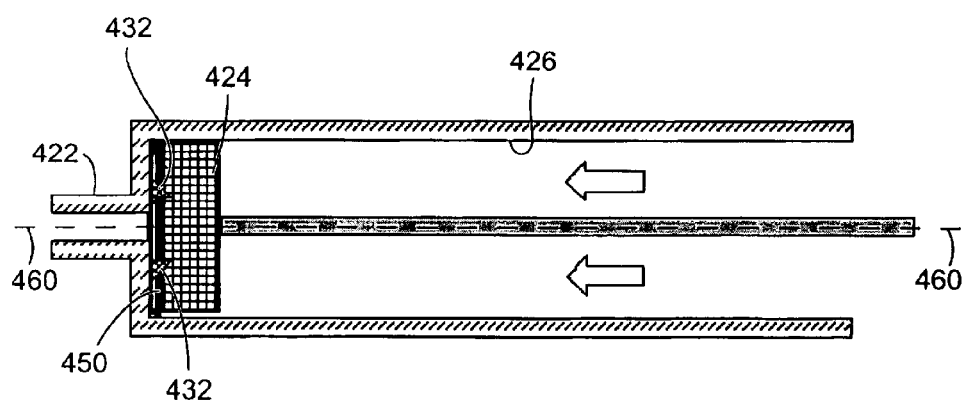

Referring to FIGS. 8A–8C, operation of the syringe of Mode IV will be described. Preferably, the second chamber contents 452 is contained within the bag 450 and the remaining tube volume forms the first chamber 440 which is filled with the first chamber contents 442. Forward motion of the rear plunger 424 will push the bag 450 through the tube interior 426 thereby injecting the first chamber contents 442 (FIG. 8A). Preferably, at least one, although two barbs 432 or other sharp protrusions are shown formed on an inner front wall of the syringe within the outlet and adjacent the outlet opening 422. Barb 432 may comprise any sharp edged surface sufficient to burst or breach the bag 450 as the plunger advances it into contact therewith. At the completion of the injection of the first chamber contents 442, continued forward movement of the rear plunger 424 forces the front wall 454 of the bag against the barbs 432 thereby piercing the bag 450 and releasing the contents 452 of the bag or the second chamber. Continued forward motion of the rear plunger 424 compresses the bag 450 until the second chamber contents 452 is fully injected and the plunger stops as it butts against the protrusion and the front wall of the syringe (FIG. 8C).

As shown above, the syringe of the present invention provides an efficient vehicle for the sequential administration of two injectable substances desired to be kept unmixed prior to injection. In imaging applications, the syringe of the present invention may be used to provide a saline flush after injection of the contrast in a manual injection procedure or in existing power injector equipment without modification to the power injectors. Moreover, by providing the contrast agent and saline flush in a single syringe, the clinical benefits of the saline flush may be attained with the use of a single barrel injector thereby eliminating the need for providing the saline flush through the double barrel power injector. The syringe of the present invention further minimizes the number of syringes used during an imaging procedure and allows for the effective use of entirely of the contrast agent fill. Additionally, the prefilled syringes of the present invention prevents the problems associated with the manual preparation of syringes, including cross contamination and improper dosing.

In view of the above, several objects of the invention are achieved and other advantageous results attained. As various changes could be made in the above construction without departing from the scope of the invention, it is intended that all matter contained in the above description and in the accompanying drawings shall be interpreted as illustrative and not in any limiting senses. For example, the outlet portion has been shown in several embodiments each of which is characterized by a particular physical arrangement. One of ordinary skill in the art could imagine other physical arrangements which would be within the scope of the present invention in that they would all serve to force the intermediate disc to lose its sealing engagement with the sidewall of the syringe after the first fluid has been injected and thereby "open" the second chamber to allow the second fluid to sequentially flow around the disc and out the syringe opening. Still other alternatives could include various physical embodiments such as sloped or ramped outlet portions, or other discontinuities in the syringe. Similarly, other baffle arrangements could be envisioned by one of ordinary skill in the art and yet be within the scope of the present invention. Different sizes, shapes, arrangements, and numbers of baffles or protuberances could be used and still achieve the function of separating the baffle from the outlet opening. These alternatives are all within the teachings hereof and intended by the inventor to be considered as part of his invention.

Additionally, there could be other procedures where the sequential injection of more than two substances would be advantageous. For instance, it may be preferable in certain imaging applications to first inject saline followed by a contrast agent followed in turn by another injection of saline. It should be understood that the syringe of the present invention could so be modified with two or more intermediate discs with corresponding discontinuities formed in the outlet adapted to allow each intermediate discs to disengage from the syringe interior to allow alignment of the outlet opening with each chamber defined by the discs. Similarly, the syringe may be configured with multiple bags and outlet may be configured with barbs that are able to rupture or breach each bag sequentially to allow sequential injection of more than two substances. These alternatives too are all within the teachings hereof and intended by the inventor to be considered as part of his invention. Accordingly, the invention therefore shall be limited solely be the scope of the claims set forth below and their legal equivalents.

What is claimed is:

1. A sequential injection syringe comprising a generally cylindrical barrel portion, a plunger and an intermediate disc being disposed in a spaced apart relationship within said barrel portion, each of said plunger and disc being sized to be in sealing engagement with said barrel portion, an outlet portion disposed generally at a distal end of said syringe, said outlet portion having an outlet opening through which fluids contained within said syringe are expelled, a first chamber for containing a first fluid within said syringe formed between the outlet portion and the disc, and a second chamber for containing a second fluid within said syringe formed between the disc and the plunger, said outlet portion having a radially enlarged portion with a protrusion in the radially enlarged portion that extends into an interior of the syringe, said protrusion being adapted to engage the intermediate disc in the radially enlarged portion as the disc is advanced to the syringe outlet opening, said radially enlarged portion being dimensioned to permit tilting of the disc in the syringe interior as the protrusion engages the disc and the disc loses sealing engagement with said syringe to thereby allow the second fluid to flow through the outlet opening after the first fluid has been substantially expelled therethrough.

2. The sequential injection syringe of claim 1 wherein said radially enlarged portion has a central axis offset from a central axis of said barrel portion.

3. The sequential injection syringe of claim 1 wherein said radially enlarged portion is dimensioned to permit partial rotation of the disc in the syringe interior as the protrusion engages the disc and the disc loses sealing engagement with said syringe.

4. The sequential injection syringe of claim 1 wherein said radially enlarged portion is formed within a wall thickness of the cylindrical barrel portion of the syringe.

5. A pre-filled, sequential injection syringe comprising a generally cylindrical barrel portion, a plunger and an intermediate disc being disposed in a spaced apart relationship within said barrel portion, each of said plunger and disc being sized to be in sealing engagement with said barrel portion, an outlet portion disposed generally at a distal end of said syringe, said outlet portion having an outlet opening through which fluids contained within said syringe are expelled, a first fluid contained within said syringe and between the outlet portion and the disc, and a second fluid contained within said syringe and between the disc and the plunger, said outlet portion having a radially enlarged portion with a protrusion in the radially enlarged portion that extends into an interior of the syringe, said protrusion being adapted to engage the intermediate disc in the radially enlarged portion as the disc is advanced to the syringe opening, said radially enlarged portion being dimensioned to permit tilting of the disc in the syringe interior as the protrusion engages the disc and the disc loses sealing engagement with said syringe to thereby allow the second fluid to flow through the outlet opening after the first fluid has been substantially excelled therethrough.

6. The pre-filled, sequential injection syringe of claim 5 wherein said radially enlarged portion has a central axis offset from a central axis of said barrel portion.

7. The pre-filled, sequential injection syringe of claim 5 wherein said radially enlarged portion is dimensioned to permit partial rotation of the disc in the syringe interior as the protrusion engages the disc and the disc loses sealing engagement with said syringe.

8. The pre-filled, sequential injection syringe of claim 5 wherein said radially enlarged portion is formed within a wall thickness of the cylindrical barrel portion of the syringe.

9. A method for sequentially expelling two fluids from a single syringe without mixing of the fluids comprising the steps of:

providing the syringe with a first fluid between a syringe opening and an intermediate disc and a second fluid between the intermediate disc and a plunger, each of the disc and plunger being in sealing engagement with the syringe, said syringe having an outlet portion being disposed generally at a distal end of said syringe, said outlet portion having a radially enlarged portion with a protrusion in the radially enlarged portion that extends into an interior the syringe;

advancing the plunger and disc within the syringe to expel the first fluid;

advancing the plunger and disc within the syringe so as to engage the disc against the protrusion thereby disengaging the disc from its sealing engagement with the syringe and creating a channel around the disc from the syringe interior to the syringe opening; and continuing to advance the plunger to thereby expel the second fluid from the syringe interior around the disc through the channel and out the syringe opening.

* * * * *